US007015305B2

(12) United States Patent
Lee et al.

(10) Patent No.: US 7,015,305 B2
(45) Date of Patent: *Mar. 21, 2006

(54) PROCESS FOR PREPARING GLYCOPEPTIDE DERIVATIVES

(75) Inventors: Junning Lee, El Granada, CA (US); Jyanwei Liu, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 313 days.

This patent is subject to a terminal disclaimer.

(21) Appl. No.: 10/226,988

(22) Filed: Aug. 23, 2002

(65) Prior Publication Data

US 2003/0045457 A1 Mar. 6, 2003

Related U.S. Application Data

(60) Provisional application No. 60/314,711, filed on Aug. 24, 2001.

(51) Int. Cl.
*A61K 38/00* (2006.01)

(52) U.S. Cl. .......................... 530/317; 514/18

(58) Field of Classification Search .............. 514/8, 514/2, 38; 530/317, 322
See application file for complete search history.

(56) References Cited

U.S. PATENT DOCUMENTS

| | | | |
|---|---|---|---|
| 3,160,632 A | 12/1964 | Toy et al. |
| 4,643,987 A | 2/1987 | Nagarajan et al. |
| 4,698,327 A | 10/1987 | Nagarajan et al. |
| 5,591,714 A | 1/1997 | Nagarajan et al. |
| 5,750,509 A | 5/1998 | Malabarba et al. |
| 5,840,684 A | 11/1998 | Cooper et al. |
| 5,916,873 A | 6/1999 | Cooper et al. |
| 5,952,466 A | 9/1999 | Berglund et al. |
| 5,998,581 A | 12/1999 | Berglund et al. |
| 6,392,012 B1 | 5/2002 | Judice et al. |
| 6,444,786 B1 | 9/2002 | Judice et al. |
| 6,455,669 B1 | 9/2002 | Judice et al. |
| 6,518,242 B1 | 2/2003 | Chen et al. |
| 2002/0010131 A1 | 1/2002 | Linsell |
| 2002/0022590 A1 | 2/2002 | Leadbetter et al. |

FOREIGN PATENT DOCUMENTS

| | | |
|---|---|---|
| EP | 0 201 251 A2 | 12/1986 |
| EP | 0 273 727 | 7/1988 |
| EP | 0 376 041 B1 | 7/1990 |
| EP | 0 525 499 A1 | 2/1993 |
| EP | 0 667 353 A1 | 8/1995 |
| EP | 0 816 378 A1 | 1/1998 |
| EP | 0 873 997 A1 | 10/1998 |
| WO | WO 98/21952 | 5/1998 |
| WO | WO 99/42476 | 8/1999 |
| WO | WO 00/39156 | 7/2000 |
| WO | WO 00/59528 | 10/2000 |
| WO | 01/57071 A2 | 8/2001 |
| WO | WO 01/82971 * | 11/2001 |
| WO | WO 01/83521 A2 | 11/2001 |
| WO | WO 01/98328 A2 | 12/2001 |

OTHER PUBLICATIONS

Cooper et al., "Reductive Alkylation of Glycopeptide Antibiotics: Synthesis and Antibacterial Activity", The Journal of Antibiotics, vol. 49, No. 6, pp 575-581 ((1996).

Nagarajan et al., "Synthesis and Antibacterial Evaluation of N-Alkyl Vancomycins", The Journal of Antibiotics, vol. XLII, No. 1, pp 63-72 (1988).

Nicolaou et al., "Chemistry, Biology, and Medicine of the Glycopeptide Antibiotics", Angew Chem. Int. Ed., vol. 38, No. 15, pp 2097-2152 (1999).

Pavlov et al., "Chemical Modification of Glycopeptide Antibiotics [VC1]", Russian Journal of Bioorganic Chemistry, vol. 24, No. 9, pp 570-587 (1998).

Rodriguez et al., "Novel Glycopeptide Antibiotics: N-Alkylated Derivatives Active Against Vancomycin-Resistant Enterococci", The Journal of Antibiotics, vol. 51, No. 6, pp 560-569 (1998).

Snyder et al., "Enzymatic Deacylation of Teicoplanin Followed by Reductive Alkylation: Synthesis and Antibacterial Activity of New Glycopeptides", The Journal of Antibiotics, vol. 51, No. 10, pp 945-951 (1998).

Sorbera et al., "Telavancin Hydrochloride: Glycopeptide Antibiotic," *Drugs of the Future* 2004, 29(12): 1211-1219.

* cited by examiner

*Primary Examiner*—Bruce R. Campell
*Assistant Examiner*—B. Dell Chism
(74) *Attorney, Agent, or Firm*—Jeffrey A. Hagenah

(57) ABSTRACT

Disclosed are processes for preparing glycopeptide antibiotic derivatives having an amino-containing side chain. The multi-step process is conducted in a single reaction vessel without isolation of intermediate reaction products.

18 Claims, No Drawings

PROCESS FOR PREPARING GLYCOPEPTIDE DERIVATIVES

CROSS-REFERENCE TO RELATED APPLICATIONS

This application claims the benefit of U.S. Provisional Application No. 60/314,711, filed on Aug. 24, 2001; the entire disclosure of which is incorporated herein by reference in its entirety.

BACKGROUND OF THE INVENTION

1. Field of the Invention

This invention is directed to novel processes for preparing derivatives of glycopeptide antibiotics. More specifically, this invention is directed to multi-step processes for preparing derivatives of glycopeptide antibiotics having an amino-containing side chain, the steps being conducted in a single reaction vessel without isolation of the intermediate reaction products.

2. Background

Glycopeptides (e.g. dalbaheptides) are a well-known class of antibiotics produced by various microorganisms (see *Glycopeptide Antibiotics*, edited by R. Nagarajan, Marcel Dekker, Inc. New York (1994)). Many synthetic derivatives of such glycopeptides are also known in the art and these derivatives are typically reported to have improved properties relative to the naturally-occurring glycopeptides, including enhanced antibacterial activity. For example, WO 00/39156, published Jul. 6, 2000, describes various glycopeptide derivatives having a heteroatom-containing side chain, including derivatives having an amino-containing side chain. These amino-containing side chain derivatives are particularly useful as antibiotics and as intermediates for producing additional glycopeptide derivatives.

Accordingly, a need exists for new efficient processes which are useful for preparing glycopeptide derivatives having an amino-containing side chain.

SUMMARY OF THE INVENTION

The present invention provides novel processes for preparing derivatives of glycopeptide antibiotics having an amino-containing side chain. Among other advantages, the present process is conducted in a single reaction vessel without isolation of the intermediate reaction products, thereby generating less waste and improving the overall efficiency and yield of the process compared to previous processes.

Specifically, in one of its aspects, this invention is directed to a process for preparing a compound of formula I:

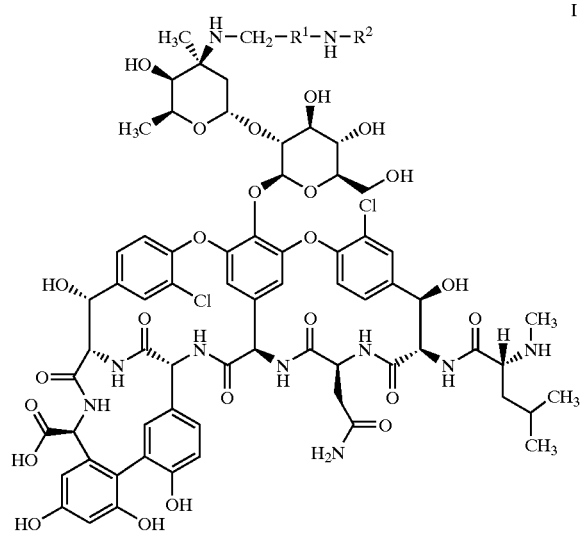

wherein $R^1$ is selected from the group consisting of $C_{1-10}$ alkylene, $C_{2-10}$ alkenylene and $C_{2-10}$ alkynylene;

$R^2$ is selected from the group consisting of $C_{1-20}$ alkyl, $C_{2-20}$ alkenyl, $C_{2-20}$ alkynyl, $C_{3-8}$ cycloalkyl, $C_{5-8}$ cycloalkenyl, $C_{6-10}$ aryl, $C_{2-9}$ heteroaryl, $C_{2-9}$ heterocyclic, $-R^a-Cy^1$, $-R^a-Ar^1-Ar^2$, $-R^a-Ar^1-R^b-Ar^2$, $-R^a-Ar^1-O-R^b-Ar^2$;

$R^a$ is selected from the group consisting of $C_{1-10}$ alkylene, $C_{1-10}$ alkenylene and $C_{1-10}$ alkynylene;

$R^b$ is selected from the group consisting of $C_{1-6}$ alkylene, $C_{1-6}$ alkenylene and $C_{1-6}$ alkynylene;

$Cy^1$ is selected from the group consisting of $C_{3-8}$ cycloalkyl, $C_{5-8}$ cycloalkenyl, $C_{6-10}$ aryl, $C_{2-9}$ heteroaryl, $C_{2-9}$ heterocyclic;

$Ar^1$ and $Ar^2$ are independently selected from $C_{6-10}$ aryl and $C_{2-9}$ heteroaryl;

wherein each aryl, heteroaryl and heterocyclic group is optionally substituted with 1 to 3 substituents independently selected from the group consisting of $C_{1-6}$ alkyl, $C_{1-6}$ alkoxy, halo, hydroxy, nitro and trifluoromethyl, and each heteroaryl and heterocyclic group contains from 1 to 3 heteroatoms selected from nitrogen, oxygen or sulfur;

or salts thereof;

the process comprising:

(a) combining vancomycin or a salt thereof, with a compound of formula II:

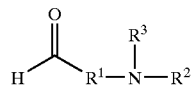

wherein $R^1$ and $R^2$ are as defined herein; and $R^3$ is a amine-labile protecting group; in the presence of a base to form a reaction mixture;

(b) acidifying the reaction mixture from step (a) with an acid;

(c) contacting the reaction mixture from step (b) with a reducing agent;

(d) contacting the reaction mixture from step (c) with an amine, to provide a compound of formula I or a salt thereof.

In the above process, $R^1$ is preferably $C_{1-6}$ alkylene. More preferably, $R^1$ is $C_{1-2}$ alkylene. Still more preferably, $R^1$ is $-CH_2-$.

$R^2$ is preferably $C_{6-14}$ alkyl. More preferably, $R^2$ is $C_{8-12}$ alkyl. Still more preferably, $R^2$ is n-decyl.

In the process of this invention, $R^3$ is an amino-protecting group which is removed by treatment with an amine (i.e., a nucleophilic amine). Preferably, $R^3$ is a group of formula (A):

W—OC(O)—         (A)

wherein W is selected from the group consisting of 9-fluorenylmethyl, 3-indenylmethyl, benz[f]inden-3-ylmethyl, 17-tetrabenzo[a,c,g,i]fluorenylmethyl, 2,7-di-tert-butyl[9-(10,10-dioxo-10,10,10,10-tetrahydrothioxanthyl)]methyl, 1,1-dioxobenzo[b]thiophene-2-ylmethyl, wherein the 9-fluorenylmethyl group is optionally substituted with 1 to 3 substitutents selected from the group consisting of $C_{1-6}$ alkyl, halo, nitro and sulfo.

Preferably, W is 9-fluorenylmethyl, wherein the 9-fluorenylmethyl group is optionally substituted with 1 to 3 substitutents selected from the group consisting of $C_{1-6}$ alkyl, halo, nitro and sulfo. More preferably, W is 9-fluorenylmethyl.

In step (a) of the process of this invention, the base employed is preferably a tertiary amine. More preferably, the base is diisopropylethylamine.

In step (b), the acid employed is preferably trifluoroacetic acid or acetic acid.

In step (c), the reducing agent is preferably an amine/borane complex. More preferably, the reducing agent is pyridine/borane or tert-butylamine/borane.

In step (d), the amine employed is preferably ammonium hydroxide or a primary amine. More preferably, the amine is ammonium hydroxide, methylamine or tert-butylamine.

DETAILED DESCRIPTION OF THE INVENTION

This invention relates to novel processes for preparing glycopeptide derivatives having an amino-containing side chain. When describing such processes, the following terms have the following meanings, unless otherwise indicated.

Definitions

The term "alkyl" refers to a monovalent saturated hydrocarbon group which may be linear or branched. Unless otherwise defined, such alkyl groups typically contain from 1 to 20 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 20 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 20 carbon atoms. Representative alkynyl groups include, by way of example, ethynyl, n-propynyl, n-but-2-ynyl, n-hex-3-ynyl and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenylene" refers to a divalent unsaturated hydrocarbon group which may be linear or branched and which has at least one, and typically 1, 2 or 3, carbon-carbon double bonds. Unless otherwise defined, such alkenylene groups typically contain from 2 to 10 carbon atoms. Representative alkenylene groups include, by way of example, ethene-1,2-diyl, prop-1-ene-1,2-diyl, prop-1-ene-1,3-diyl, but-2-ene-1,4-diyl, and the like.

The term "alkynylene" refers to a divalent unsaturated hydrocarbon group which may be linear or branched and which has at least one, and typically 1, 2 or 3, carbon-carbon triple bonds. Unless otherwise defined, such alkynylene groups typically contain from 2 to 10 carbon atoms. Representative alkynylene groups include, by way of example, ethyne-1,2-diyl, prop-1-yne-1,2-diyl, prop-1-yne-1,3-diyl, but-2-yne-1,4-diyl, and the like.

The term "alkoxy" refers to a group of the formula —O—R, where R is alkyl as defined herein. Representative alkoxy groups include, by way of example, methoxy, ethoxy, n-propoxy, isopropoxy, n-butoxy, sec-butoxy, isobutoxy, tert-butoxy and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "cycloalkenyl" refers to a monovalent unsaturated carbocyclic hydrocarbon group having at least one carbon-carbon double bond in the carbocyclic ring. Unless otherwise defined, such cycloalkenyl groups typically contain from 5 to 10 carbon atoms. Representative cycloalkenyl groups include, by way of example, cyclopent-3-en-1-yl, cyclohex-1-en-1-yl and the like.

The term "halo" refers to fluoro, chloro, bromo and iodo; preferably, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocycle" or "heterocyclic" refers to a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "vancomycin" is used herein in its art recognized manner to refer to the glycopeptide antibiotic known as vancomycin. See, for example, R. Nagarajan, "Glycopeptide Anitibiotics", Marcel Dekker, Inc. (1994) and references cited therein. The designation "$N^{van}$—" refers to substitution at the vancosamine nitrogen atom of vancomycin. This position is also referred to as the N3" position of vancomycin.

The term "salt" when used in conjunction with a compound referred to herein refers to a salt of the compound derived from an inorganic or organic base or from an inorganic or organic acid. Salts derived from inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "protecting group" or "blocking group" refers to a group which, when covalently attached to a function group such as an amino, hydroxyl, thiol, carboxyl, carbonyl and the like, prevents the functional group from undergoing undesired reactions but which permits the function group to be regenerated (i.e., deprotected or unblocked) upon treatment of the protecting group with a suitable reagent. Representative protecting groups are disclosed, for example, in T. W. Greene and P. G. M. Wuts, "Protective Groups in Organic Synthesis" $3^{rd}$ Ed., 1999, John Wiley and Sons, N.Y.

The term "amine-labile protecting group" refers to a protecting group which is removed upon treatment with a suitable amine.

Process Conditions

The process of the present invention is conducted in a single reaction vessel in multiple steps. The first of these steps involves combining one equivalent of vancomycin or a salt thereof, with one or more equivalents of an aldehyde of formula II:

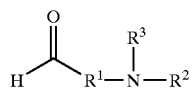

wherein $R^1$, $R^2$ and $R^3$ are as defined herein, and an excess of a suitable base in an inert diluent to form a reaction mixture. Preferably, from about 1 to about 2 equivalents of the aldehyde are used in this step of the process; more preferably, about 1.1 to about 1.2 equivalents. In this reaction mixture, a mixture of imines and/or hemiaminals is believed to be formed between the aldehyde and the basic nitrogen atoms of vancomycin, i.e., the vancosamine nitrogen atom and the N-terminal (leucinyl) nitrogen atom.

This first step of the present process is typically conducted at a temperature ranging from about 0° C. to about 75° C., preferably at ambient temperature (i.e., about 20–25° C.) for about 1 to about 24 hours, preferably for about 6 to 12 hours, or until formation of the imine and/or hemiaminal is substantially complete.

This step of the process and the remaining steps are typically conducted in an inert diluent. Preferably, the inert diluent is N,N-dimethylformamide, N,N-dimethylacetamide, N-methylpyrrolidinone, acetonitrile/water, and the like or mixtures thereof.

Any suitable base may be employed in this step to neutralize the vancomycin salt and to facilitate formation of the imine and/or hemiaminal, including organic bases, such as amines, alkali metal carboxylate salt (i.e., sodium acetate and the like) and inorganic bases, such as alkali metal carbonates (i.e., lithium carbonate, potassium carbonate and the like). Preferably, the base used in this step is a tertiary amine including, by way of illustration, triethylamine, diisopropylethylamine, N-methylmorpholine, and the like. A preferred base is diisopropylethylamine. The base is typically employed in a molar excess relative to vancomycin. Preferably, the base is used in an amount ranging from about 1.5 to about 3 equivalents based on vancomycin; more preferably, about 1.8 to 2.2 equivalents.

When formation of the imine and/or hemiaminal mixture is substantially complete, the reaction mixture is acidified with an excess of acid. Any suitable acid may be employed in this step of the process including, by way of illustration, carboxylic acids (e.g. acetic acid, trichloroacetic acid, citric acid, formic acid, trifluoroacetic acid, methanesulfonic acid, toluenesulfonic acid and the like), mineral acids (e.g. hydrochloric acid, sulfuric acid, or phosphoric acid), and the like. Preferably, the acid employed in this step is trifluoroacetic acid or acetic acid. The acid is typically added in a molar excess relative to vancomycin (and the base). Preferably, the acid is used in an amount ranging from about 3 to about 6 equivalents based on vancomycin; more preferably, about 3.5 to 5.5 equivalents.

While not wishing to be limited by theory, it is believed that the acid selectively hydrolyzes the imine and/or hemiaminal formed at the N-terminal amine of vancomycin in preference to the imine and/or hemiaminal formed at the vancosamine nitrogen atom. This acidification step is typically conducted at a temperature ranging from about 0° C. to about 30° C., preferably at about 25° C., for about 0.25 to about 2.0 hours, preferably for about 0.25 to about 1.5 hours. Preferably, a polar, protic solvent is added during this step including, by way of example, methanol, ethanol, propanol, isopropanol, butanol, ethylene glycol, and the like. Alternatively, a mixed polar protic/non-protic solvent may be used, such as methanol/tetrahydrofuran, methanol/1,2-dimethoxyethane and the like After the acidification step, the reaction mixture is then contacted with a reducing agent to reduce the imine and/or hemiaminal. Any suitable reducing agent can be employed in this step of the process which is compatible with the functionality present in the glycopeptide. For example, suitable reducing agents include sodium borohydride, sodium cyanoborohydride, zinc borohydride, sodium triacetoxyborohydride, pyridine/borane, tert-butylamine/borane, N-methylmorpholine/borane, ammonia/borane, dimethylamine/borane, triethylamine/borane, trimethylamine/borane, and the like. Preferred reducing agents are amine/borane complexes such as pyridine/borane and tert-butylamine/borane.

This reduction step of the process is typically conducted at a temperature ranging from about 0° C. to about 30° C., preferably at about 25° C., for about 0.5 to about 24 hours, preferably for about 1 to about 6 hours, or until the reduction is substantially complete. Preferably, a polar, protic solvent is present during this reduction step. The polar, protic solvent is preferably added during the acidification step described above.

In contrast to prior procedures, the product of the reductive alkylation process is not isolated but the reaction mixture is contacted with an amine to remove the protecting group (i.e., $R^3$) from the intermediate product. Any suitable amine may be used in this step of the process. Representative amines suitable for use include, by way of example, methylamine, ethylamine, tert-butylamine, triethylamine, piperidine, morpholine, ammonium hydroxide, and the like. Preferred amines are methylamine, tert-butylamine and ammonium hydroxide.

This deprotection step of the process is typically conducted at a temperature ranging from about 0° C. to about 60° C., preferably at about 40° C. to about 45° C., for about 2 to about 60 hours, preferably for about 3 to about 10 hours, or until the reaction is substantially complete. The resulting compound of formula I is readily isolated and purified by conventional procedures, such as precipitation and/or reverse-phase HPLC.

The aldehydes of formula II employed in the process of the present invention are well-known in the art and are either commercially available or can be prepared by conventional procedures using commercially available starting materials and conventional reagents. For example, see WO 00/39156, published on Jul. 6, 2000, which describes various methods for preparing such aldehydes.

Among other advantages, the process of the present invention provides for improved selectivity, i.e., reductive alkylation at the vancosamine amino group is favored over reductive alkylation at the N-terminus (e.g., the leucinyl group) by at least 10:1, more preferably 20:1. Additionally, because the multi-step process is conducted in a single reaction vessel without isolation of the reaction intermediates, the process of the present invention is more efficient, provides a higher yield and generates less waste then previous processes.

The glycopeptide derivatives produced by the process of this invention are useful as antibiotics and as intermediates for the production of antibiotics. See, for example, U.S. patent application Ser. No. 09/470,209, filed Dec. 22, 1999; and U.S. patent application Ser. No. 09/847,042, filed May 1, 2001; the disclosures of which are incorporated herein by reference in their entirety.

Additional details of the process of this invention are described in the following Examples which are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius (° C.).

DIPEA=diisopropylethylamine
DMF=N,N-dimethylformamide
DMSO=dimethyl sulfoxide
eq.=equivalent
Fmoc=9-fluorenylmethoxycarbonyl
TFA=trifluoroacetic acid In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

Example A

Preparation of N-Fmoc-Decylaminoacetaldehyde.

Step A—Preparation of N-Fmoc-2-(n-Decylamino)ethanol 2-(n-Decylamino)ethanol (2.3 g, 11 mmol, 1.1 eq) and DIPEA (2.0 mL, 11 mmol, 1.1 eq) were dissolved in methylene chloride (15 mL) and cooled in an ice bath. 9-Fluorenylmethyl chloroformate (2.6 g, 10 mmol, 1.0 eq) in methylene chloride (15 ml) was added, the mixture stirred for 30 minutes then washed with 3 N hydrochloric acid (50 mL) twice and saturated sodium bicarbonate (50 mL). The organics were dried over magnesium sulfate, and the solvents removed under reduced pressure. N-Fmoc-2-(n-decylamino)ethanol (4.6 g, 11 mmol, 108%) was used without further purification.

Step B—Preparation of N-Fmoc-2-(n-Decylamino)acetaldehyde

To a solution of oxalyl chloride (12.24 mL) and methylene chloride (50 mL) at −35 to −45° C. was added DMSO (14.75 g) in methylene chloride (25 mL) over 20 minutes. The reaction mixture was stirred for 10 minutes at −35 to −45° C. A solution of N-Fmoc-2-(n-decylamino)ethanol (20.0 g) in methylene chloride (70 mL) was added over 25 minutes and then stirred 40 minutes at −35 to −45° C. Triethylamine (21.49 g) was then added and the mixture stirred for 30 minutes at −10 to −20° C. The reaction mixture was quenched with water (120 mL) followed by concentrated sulfuric acid (20.0 g) while maintaining the internal temperature at 0–5° C. The organic layer was isolated and washed with 2% sulfuric acid (100 mL) followed by water (2×100 mL). The organic solution was distilled under vacuum at 60° C. to about 100 mL. Heptane (100 mL) was added, the temperature of the oil bath raised to 80° C. and the distillation was continued until the residual volume was 100 mL. More heptane (100 mL) was added and the distillation repeated to a volume of 100 mL. The heating bath was replaced with a cold water bath at 15° C. The bath was cooled slowly to 5° C. over 20 minutes to start the precipitation of the product. The slurry was then cooled to −5 to −10° C. and the slurry was stirred for 2 hours. The solid was then collected on a Buchner funnel and washed with cold (−5° C.) heptane (2×15 mL). The wet solid was dried in vacuo to yield the title aldehyde.

Example 1

Preparation of $N^{van}$-2-(n-Decylamino)ethyl Vancomycin Hydrochloride

To a stirred mixture of 20 g (13.46 mmol) of vancomycin hydrochloride and 6.526 g (15.48 mmol) of N-Fmoc-2-(n-decylamino)acetyldehyde was added 130 mL of N,N-dimethylformamide and 4.7 mL (26.92 mmol) of N,N-diisopropylethylamine. The resulting mixture was stirred at room temperature under nitrogen for 15 hours, and 75 mL of methanol and 4.15 mL of trifluoroacetic acid (53.84 mmol) were added at 0° C. successively. The mixture was stirred for 1 hour and 1.93 mL (15.48 mmol) of borane-pyridine complex was added. The resulting mixture was stirred for 4 hours at 0° C., and 80 mL (161.52 mmol) of a 2 M methylamine in methanol was added. The resulting mixture was warmed to room temperature and stirred for 50 hours, cooled to 0° C., and water (350 mL) was added dropwise. The mixture was acidified to pH 3.60 by slow addition of 11 mL of concentrated hydrochloric acid, and precipitation occurred. The mixture was stirred for another 30 min and then it was filtered through a Buchner funnel. The resulting wet cake was washed with water (2×200 mL) and dried in vacuo for 16 hours to give 9.8 g of crude $N^{van}$-2-(n-decylamino)ethyl vancomycin hydrochloride.

Example 2

Preparation of $N^{van}$-2-(n-Decylamino)ethyl Vancomycin Hydrochloride

To a 1 L three-necked round bottom flask equipped with a mechanical stirrer, a thermometer and a nitrogen bubbler was added 180 mL of N,N-dimethylformamide (DMF). While stirring, 6.75 g (0.0160 mol) of N-Fmoc-2-(n-decylamino)-acetyldehyde and 25 g (0.0168 mol) of vancomycin hydrochloride were added successively. The addition funnel was rinsed with 20 mL of DMF; and then 5.85 mL (0.0336 mol) of N,N-diisopropylethylamine were added. The resulting mixture was stirred at room temperature under nitrogen for 6–8 hours while maintaining the temperature at 20–25° C. Methanol (95 mL) was added in one portion and then 5.2 mL (0.0672) of trifluoroacetic acid were added within 1 minute. The mixture was stirred for 0.25 hours and then 1.39 g (0.016 mol) of borane-tert-butyl amine complex were added to the reaction mixture in one portion. The addition funnel was rinsed with 5 mL of methanol, and the resulting mixture was stirred for 2 hours at room temperature. tert-Butylamine (10.6 mL, 0.101 mol) was added in one portion and the resulting mixture was stirred at 40–42° C. for about 7 hours. The reaction mixture was then cooled to room temperature and 140 mL of 0.5 N HCl were added, followed by 600 mL o f a 10% brine solution at room temperature. The resulting mixture was stirred for 2 hours at 20–25° C., and then cooled to 10° C. and stirred for 1 hour. The resulting precipitate is collected using a 12.5 cm Buchner funnel by filtering the reaction mixture over a period of about 90 min. The wet cake was washed with cold water (2×50 mL) and sucked dry for 5 hours. The resulting material was added to 200 mL of acetonitrile while stirring to 2 hours at 20–25° C. The resulting slurry was filtered through an 8 cm Buchner funnel and the collected wet cake was washed with acetonitrile (2×25 mL) and dried under house vacuum (about 25 mm Hg) for 13 hours to afford 31.1 g of crude $N^{van}$-2-(n-decylamino)ethyl vancomycin hydrochloride.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:
1. A process for preparing a compound of formula I:

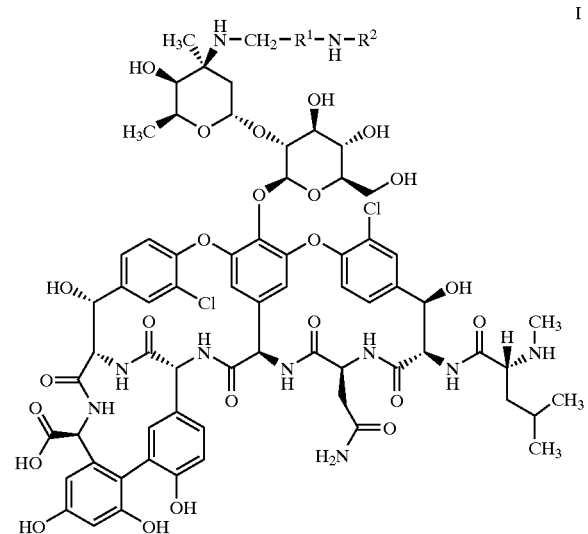

wherein
$R^1$ is selected from the group consisting of $C_{1-10}$ alkylene, $C_{2-10}$ alkenylene and $C_{2-10}$ alkynylene;
$R^2$ is selected from the group consisting of $C_{1-20}$ alkyl, $C_{2-20}$ alkenyl, $C_{2-20}$ alkynyl, $C_{3-8}$ cycloalkyl, $C_{5-8}$ cycloalkenyl, $C_{6-10}$ aryl, $C_{2-9}$ heteroaryl, $C_{2-9}$ heterocyclic, —$R^a$-$Cy^1$, —$R^a$-$Ar^1$-$Ar^2$, —$R^a$-$Ar^1$-$R^b$-$Ar^2$, —$R^a$-$Ar^1$-O—$R^b$-$Ar^2$;
$R^a$ is selected from the group consisting of $C_{1-10}$ alkylene, $C_{1-10}$ alkenylene and $C_{1-10}$ alkynylene;
$R^b$ is selected from the group consisting of $C_{1-6}$ alkylene, $C_{1-6}$ alkenylene and $C_{1-6}$ alkynylene;
$Cy^1$ is selected from the group consisting of $C_{3-8}$ cycloalkyl, $C_{5-8}$ cycloalkenyl, $C_{6-10}$ aryl, $C_{2-9}$ heteroaryl, $C_{2-9}$ heterocyclic;
$Ar^1$ and $Ar^2$ are independently selected from $C_{6-10}$ aryl and $C_{2-9}$ heteroaryl;
wherein each aryl, heteroaryl and heterocyclic group is optionally substituted with 1 to 3 substituents independently selected from the group consisting of $C_{1-6}$ alkyl, $C_{1-6}$ alkoxy, halo, hydroxy, nitro and trifluoromethyl, and each heteroaryl and heterocyclic group contains from 1 to 3 heteroatoms selected from nitrogen, oxygen or sulfur;
or salts thereof;
the process comprising:
(a) combining vancomycin or a salt thereof, with a compound of formula II:

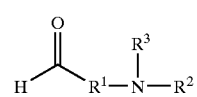

wherein $R^1$ and $R^2$ are as defined herein; and $R^3$ is a amine-labile protecting group; in the presence of a base to form a reaction mixture;
(b) acidifying the reaction mixture from step (a) with an acid;

(c) contacting the reaction mixture from step (b) with a reducing agent;

(d) contacting the reaction mixture from step (c) with an amine, to provide a compound of formula I or a salt thereof.

2. The process according to claim 1, wherein $R^1$ is $C_{1-6}$ alkylene.

3. The process according to claim 2, wherein $R^1$ is —$CH_2$—.

4. The process according to claim 1, wherein $R^2$ is $C_{6-14}$ alkyl.

5. The process according to claim 4, wherein $R^2$ is n-decyl.

6. The process according to claim 1, wherein $R^3$ is a group of formula (A):

wherein W is selected from the group consisting of 9-fluorenylmethyl, 3-indenylmethyl, benz[f]inden-3-ylmethyl, 17-tetrabenzo[a,c,g,i]fluorenylmethyl, 2,7-di-tert-butyl[9-(10,10-dioxo-10,10,10,10-tetrahydrothioxanthyl)]methyl, 1,1-dioxobenzo[b]thiophene-2-ylmethyl, wherein the 9-fluorenylmethyl group is optionally substituted with 1 to 3 substitutents selected from the group consisting of $C_{1-6}$ alkyl, halo, nitro and sulfo.

7. The process according to claim 6, wherein W is 9-fluorenylmethyl, wherein the 9-fluorenylmethyl group is optionally substituted with 1 to 3 substitutents selected from the group consisting of $C_{1-6}$ alkyl, halo, nitro and sulfo.

8. The process according to claim 7, wherein W is 9-fluorenylmethyl.

9. The process according to claim 1, wherein the base in step (a) is a tertiary amine.

10. The process according to claim 9, wherein the base in step (a) is diisopropylethylamine.

11. The process according to claim 1, wherein the acid in step (b) is trifluoroacetic acid or acetic acid.

12. The process according to claim 1, wherein the reducing agent in step (c) is amine/borane complex.

13. The process according to claim 12, wherein the reducing agent in step (c) is pyridine/borane or tert-butylamine/borane.

14. The process according to claim 1, wherein the amine in step (d) is ammonium hydroxide or a primary amine.

15. The process according to claim 14, wherein the amine in step (d) is ammonium hydroxide, methylamine or tert-butylamine.

16. The process according to claim 15, wherein the amine in step (d) is tert-butylamine.

17. The process according to claim 1, wherein:

$R^1$ is —$CH_2$—;

$R^2$ is n-decyl;

$R^3$ is W—OC(O)—, where W is 9-fluorenylmethyl;

the base in step (a) is diisopropylethylamine;

the acid in step (b) is trifluoroacetic acid or acetic acid;

the reducing agent in step (c) is pyridine/borane or tert-butylamine/borane;

and the amine in step (d) is ammonium hydroxide, methylamine or tert-butylamine.

18. The process according to claim 17, wherein the reducing agent in step (c) is tert-butylamine/borane; and the amine in step (d) is tert-butylamine.

* * * * *